United States Patent [19]

McGredy

[11] Plant 4,281

[45] Jul. 18, 1978

[54] ROSE PLANT

[76] Inventor: Samuel D. McGredy, P.O. Box 14-100, Auckland, New Zealand

[21] Appl. No.: 834,504

[22] Filed: Sep. 19, 1977

[51] Int. Cl.[2] ..... A01H 5/00
[52] U.S. Cl. ..... Plt./12
[58] Field of Search ..... Plt./11-12

*Primary Examiner*—Robert E. Bagwill
*Attorney, Agent, or Firm*—Vincent G. Gioia

[57] ABSTRACT

The present invention relates to a new and distinct variety of rose plant of the hybrid tea rose class, which was originated by my crossing as seed parent the rose known as "Peer Gynt" and the rose known as "Brazilia" as pollen parent.

1 Drawing Figure

1

Among the novel characteristics possessed by this new variety which distinguish it from its parents and all other varieties of which I am aware are: (1) large high centered blooms with reflexing petals producing a spiral, circular outline upon opening, (2) unusual bicolored flowers with yellow overcast with light red petal tops and yellow reverse with yellow tinting on the light red surface at the petal base, (3) thick petals of unusually good substance, and (4) a very vigorous plant, upright growing and producing long stems. Asexual reproduction by budding of the new variety as performed in Clackamas County, Oregon, shows that the foregoing and other distinguishing characteristics come true to form and are established and transmitted through succeeding propagations.

The new and improved rose variety which I have developed is a fine hybrid tea rose of unusual coloring due to different colors of the undersides of the petals than the top sides. This difference produces an attractive shrimp pink tonality upon opening which is especially appealing because of the physical structure of the flowers. The petals reflex so as to produce a spiral, circular outline. Another outstanding feature is that the hybrid tea blooms are borne singly on long cutting stems and the petals are thick and with very good substance. The plant is very vigorous and presents the high centered blooms well on long cutting stems.

The accompanying drawing shows typical specimens of the vegetative growth and flowers of the new variety in different stages of development and depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "13C" is plate 13C of the Royal Horticultural Society Color Chart.

Parentage:
- *Seed parent.*—"Peer Gynt".
- *Pollen parent.*—"Brazilia".

Class: Hybrid tea.

The following observations are made of specimens grown at Clackamas County, Ore. during the month of August.

2

FLOWER

Blooming habit: Continuous.

Bud:
- *Size.*—Large.
- *Form.*—High centered, reflexed.
- *Color.*—When sepals first divide — 12D. When petals begin to unfurl — 13C. When half-blown: inside of petals — yellow 13C overcast and edged with red 52A. Reverse side of petals — 13C.
- *Sepals.*—Fancy, longer than bud; green 144C with sparse reddish glandular hairs.
- *Peduncle.*—Length — medium. Aspect — straight. Strength — heavy. Color — green 144B overcast red 180B.

Bloom:
- *Size.*—Average size when fully expanded — about 4 inches.
- *Borne.*—Singly.
- *Form.*—High centered blooms unfolding spirally producing circular outline.
- *Petalage.*—Number of petals — about 40.
- *Color.*—(*during first two days*). —Inner petals at center of flower — 13C flushed and edged 52A. Outer petals — 13C flushed and edged 52A. Base of petals (point of attachment) — 13A. Reverse of petals — 13B. General tonality from a distance — bicolored light red and yellow.
- *Color change.*—As bloom ages — surface 11C overcast 51B with reverse 11C producing a general shrimp pink tonality upon aging.

Petals:
- *Texture.*—Thick, heavy substance.
- *Appearance.*—Luminous.
- *Form.*—High centered.
- *Arrangement.*—Spiraled.
- *Petaloids in center.*—Few.
- *Persistence.*—Long lasting, drop off cleanly.
- *Fragrance.*—Sweet, spicy.
- *Lasting quality.*—Very good on plant and as cut flower.

REPRODUCTIVE ORGANS

Stamens, filaments and anthers:
- *Arrangement.*—Regular arrangement.
- *Color.*—13B — 13C.

Pollen: Color — 13B.

Styles: Uneven, shorter than average.

Stigmas: Color 51C, stigmatic surface — 11C.

Hips:

*Shape.*—Ovoid.

*Size.*—Large.

*Color.*—Yellow flushing rust when mature.

*Do seeds protrude?.*—Yes.

PLANT

Form: Upright.

Growth: Very vigorous and long stemmed, attaining height of 4½ feet.

Folliage: Compound, 5 leaflets.

*Size.*—Large.

*Quantity.*—Abundant, close set.

*Color.*—New foliage: Upper side — near to 153D. Under side — near to 145B. Old foliage: Upper side — 137A. Under side — 138B.

*Shape.*—Oval, acuminate.

*Texture.*—Glossy. Under side — dull.

*Edge.*—Finely serrated.

*Leaf stem.*—Color — near to 137C. Under side — near to 138B.

*Stipules.*—Long, extending almost to first leaflets.

*Resistance to disease.*—Blackspot — excellent. Mildew — excellent. Rust — excellent.

Wood:

*New wood.*—Color — near 144. Bark — smooth, shiny.

*Old Wood.*—Color — 152A. Bark — smooth.

Thorns:

*Thorns.*—Quantity: medium number of large thorns interposed with many tiny ones. On laterals — few large thorns. Form — slight. Length — 6mm. Color — when young — 144B; when mature — 172C. Position — irregular.

*Prickles.*—Profuse on many stalks and few on laterals.

Winter Hardiness: Average winter hardiness.

I claim:

1. A new and distinct variety of rose plant of the hybrid tea class, substantially as shown and described, characterized particularly by high centered, attractive bicolored flowers with thick petals and good substance, borne primarily singly and having a spiral, circular outline, and a vigorous, upright growing plant habit, with long stems and large foliage, and of particularly good disease resistance.

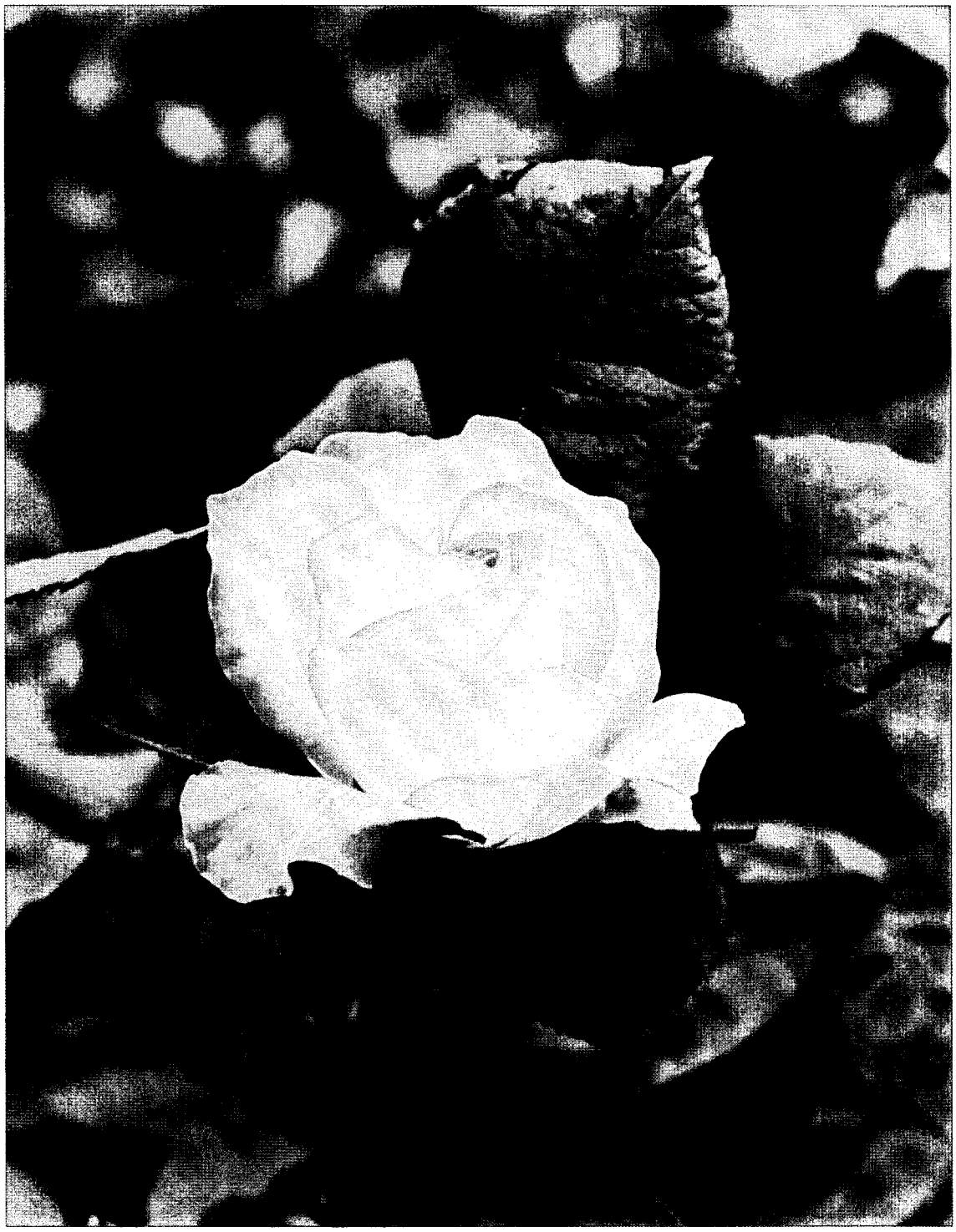

* * * * *